(12) United States Patent
Dafni

(10) Patent No.: US 7,042,977 B2
(45) Date of Patent: May 9, 2006

(54) DOSE CONTROL IN CT-IMAGES

(75) Inventor: Ehud Dafni, Caesaria (IL)

(73) Assignee: Koninklijke Philips Electronics N.V., Eindhoven (NL)

(*) Notice: Subject to any disclaimer, the term of this patent is extended or adjusted under 35 U.S.C. 154(b) by 13 days.

(21) Appl. No.: 10/488,643

(22) PCT Filed: Sep. 5, 2001

(86) PCT No.: PCT/IL01/00838

§ 371 (c)(1),
(2), (4) Date: Mar. 4, 2004

(87) PCT Pub. No.: WO03/022016

PCT Pub. Date: Mar. 13, 2003

(65) Prior Publication Data

US 2004/0247071 A1 Dec. 9, 2004

(51) Int. Cl.
*G21K 1/12* (2006.01)
*G01N 23/00* (2006.01)
*A61B 6/00* (2006.01)

(52) U.S. Cl. .................. 378/16; 378/4; 378/8

(58) Field of Classification Search ........... 378/16, 378/4, 8, 15, 18, 19, 20, 21, 22, 23, 25, 26, 378/108, 145
See application file for complete search history.

(56) References Cited

U.S. PATENT DOCUMENTS

| | | | | |
|---|---|---|---|---|
| 5,345,381 A | * | 9/1994 | Wallschlaeger | 378/15 |
| 5,400,378 A | * | 3/1995 | Toth | 378/16 |
| 5,822,393 A | * | 10/1998 | Popescu | 378/108 |
| 6,072,851 A | * | 6/2000 | Sivers | 378/15 |

FOREIGN PATENT DOCUMENTS

WO    WO 98/33361    *    7/1998

* cited by examiner

Primary Examiner—Edward J. Glick
Assistant Examiner—Irakli Kiknadze
(74) Attorney, Agent, or Firm—Thomas M. Lundin

(57) ABSTRACT

A method for determining a modulation function for modulating intensity of X-rays provided by an X-ray source of a CT-system for CT-imaging a slice of a region a person's body, the method comprising: acquiring X-ray attenuation data for a first substantially anterior-posterior or lateral view of the slice; determining a first maximum X-ray attenuation from the attenuation data; determining a length of a projection of the slice along an axis in the plane of the slice that is substantially orthogonal to the view angle using the attenuation data; determining a second maximum X-ray attenuation for a second view orthogonal to the first view based on the determined length; and using the first and second attenuation maxima to determine the modulation function.

8 Claims, 2 Drawing Sheets

DOSE CONTROL IN CT-IMAGES

FIELD OF THE INVENTION

The present invention relates to computerized tomography (CT) X-ray imaging, and in particular to controlling radiation exposure of a patient to X-rays during CT-imaging of a region of the person's body.

BACKGROUND OF THE INVENTION

In CT X-ray imaging of a patient, X-rays are used to image internal structure and features of a region of the person's body. The imaging is performed by a CT-imaging system that images internal structure and features of a plurality of contiguous relatively thin planar slices of the body region using X-rays.

The CT-imaging system generally comprises an X-ray source that provides a planar, fan-shaped X-ray beam and an array of closely spaced X-ray detectors that are coplanar with the fan beam and face the X-ray source. The X-ray source and array of detectors are mounted in a gantry so that a person being imaged with the system, generally lying on an appropriate support couch, can be positioned between the X-ray source and the array of detectors. The gantry and couch are moveable with respect to each other so that the X-ray source and detector array can be positioned axially at desired locations along the patient's body. In addition, the gantry, or X-ray source supported in the gantry, is rotatable around the axial direction so that the X-ray source can be positioned at desired angles, referred to as "view angles", around the patient's body.

To image a slice in a region of a patient's body, the X-ray source is positioned at the axial position of the slice and the X-ray source is rotated around the slice to illuminate the slice with X-rays from a plurality of different view angles. At each view angle, detectors in the array of detectors measure intensity of X-rays from the source that pass through the slice. The intensity of X-rays measured by a particular detector in the array of detectors is a function of an amount by which X-rays are attenuated by material in the slice along a path length from the X-ray source, through the particular slice, to the detector. The measurement provides information on composition and density of tissue in the slice along the path-length.

For example, if intensity sensed by an "n-th" detector in the array of detectors when the X-ray source is located at a view angle $\theta$ is represented by $I(n,\theta)$ then $I(n,\theta)=I_O\exp(-\int\mu(l)dl)$. In the expression for $I(n,\theta)$, $I_O$ is intensity of X-rays with which the X-ray source illuminates the slice, integration over l represents integration over a path through material in the slice along a direction from the X-ray source to the n-th detector and $\mu(l)$ is an absorption coefficient for X-rays per unit path-length in the material at position l along the path. (Dependence of the integral on n and $\theta$ is not shown explicitly and is determined through dependence of the length and direction of the path-length l on n and $\theta$.)

From $I_O$ and the sensed $I(n,\theta)$ an amount by which X-rays are attenuated along path-length l and a value for $\int\mu(l)dl$ can be determined. The attenuation measurement provided by the n-th detector at the view angle $\theta$ therefore provides a value for the line integral of the absorption coefficient along a particular path length through the slice which is determined by $\theta$ and the known position of the n-th detector relative to the X-ray source.

It is convenient to represent the line integral, hereinafter referred to as an "absorption integral", of the absorption coefficient along a path through a slice by the symbol $A(n,\theta,z)$ so that $A(n,\theta,z)=\int\mu(l)dl$. In the expression for $A(n,\theta,z)$, z represents an axial coordinate of the slice as measured along a z-axis of a coordinate system for which the z-axis is coincident with the axial direction around which the X-ray source rotates. For convenience, an x-axis and y-axis of the coordinate system are assumed to be horizontal and vertical axes respectively and view angle $\theta$ is an azimuth angle about the z-axis measured relative to the y-axis. At a view angle of 0° the X-ray source is directly above the patient and X-rays from the X-ray source pass through the patients body from front to back, i.e. in an anterior-posterior direction. At a view angle of 90° the X-ray source is at a side of the patient and X-rays from the X-ray source pass through the patient from one side to the other of the patient's body, i.e. in a lateral direction.

The set of attenuation measurements for a slice provided by all the detectors in the detector array at a particular view angle $\theta$ is referred to as a view. The set of attenuation measurements from all the views of the slice is referred to as a "projection" of the slice. Values for the absorption integral $A(n,\theta,z)$ provided by data from the projection of the slice are processed using algorithms known in the art to provide a map of the absorption coefficient $\mu$ as a function of position in the slice. Maps of the absorption coefficient for the plurality of contiguous slices in the region of the patient's body can be used to provide a three dimensional map of the absorption coefficient for the region. The map is used to display and identify internal organs and features of the region.

In some CT systems, to image a region of a patient, the patient is moved stepwise in the z direction to "step" the region through the gantry that houses the X-ray source and detector array. Following each step, the X-ray source is rotated through 360 degrees or (180+$\Delta$) degrees, where $\Delta$ is an angular width of the fan beam provided by the X-ray source, to acquire a projection of a slice of the region. In some CT systems a "spiral scan" of a patient is performed in which the region of the patient is steadily advanced through the gantry while the X-ray source simultaneously rotates around the patient and projections of slices in the region are acquired "on the fly".

For safety and health reasons it is desirable to minimize a dose of X-ray radiation that a patient receives when the patient is imaged using a CT-system. However, a signal to noise ratio (SNR) of an X-ray intensity measurement provided by a detector in the CT-system decreases as a number of X-ray photons reaching the detector decreases. Therefore, if intensity $I_O$ of X-rays used to acquire a CT-image is too low or attenuation of the X-rays after passing through the patient is too high, accuracy of absorption measurements decreases and quality of a CT-image provided by the CT-system is degraded.

Various methods are known in the art for reducing radiation exposure of a patient to X-rays during acquisition of a CT-image of a region of the patient's body without unduly compromising quality of the CT-image. The methods generally involve modulating $I_O$ of the X-ray source that provides the X-rays, in accordance with an appropriate function, so that $I_O$ is greater for views for which attenuation of X-rays is relatively high and smaller for views for which X-ray attenuation is relatively low. The function used to define $I_O$ as a function of X-ray source position is hereinafter referred to as an "X-ray modulation function".

In prior art CT-systems, data for generating an appropriate X-ray modulation function for imaging a region of a patient's body is often acquired from two "reconnaissance"

scans, hereinafter referred to as "planar scans", of the region that are performed prior to imaging the region. The planar scans are used to determine a maximum attenuation, hereinafter referred to as a "peak attenuation", for X-rays in each of two generally orthogonal views for each slice of the region to be imaged. (A maximum attenuation for a view is defined as a maximum for the expression $1/\exp(-\int\mu(l)dl)$, or equivalently, a maximum for $\exp(\int\infty(l)dl)$, for the view.) The attenuation maxima in the two views are used to determine minimum intensities at which to expose the views in order to acquire attenuation data at a desired SNR.

Usually, in a first planar scan, a first view of each slice is taken at 0°, i.e. an anterior-posterior view, and in a second planar scan a view of each slice is taken at 90°, i.e. a lateral view. For one of these views a longest path length in the view is generally longer than the longest path length in any other view of the slice. For the other of these views a longest path length in the view is generally shorter than the longest path length in any of the other views of the slice. (For example, for a slice in the region of the chest the path lengths are longest for the lateral view angle and shortest for the anterior-posterior view. For a slice in the region of the head, path-lengths are longest for the anterior-posterior view and shortest for the lateral view.)

The larger of the peak attenuations determined from the two "planar" views is therefore generally larger than the peak attenuations for views of the slice at any other view angle. Similarly the smaller of the peak attenuations determined from the planar views is smaller than the peak attenuations for any other view angle of the slice. The peak attenuations from the planar views "bracket" the peak attenuations for views of the slice. If peak attenuation in a view of a slice at view angle $\theta$ is represented by $PA(\theta,z)$ for a slice at coordinate z then either $PA(0°,z) \leq PA(\theta,z) \leq PA(90°,z)$ or $PA(90°,z) \leq PA(\theta,z) \leq PA(0°,z)$.

As a result, minimum X-ray intensities required to acquire data at the two views for a desired SNR bracket minimum X-ray intensities required at any of the other views of the slice that are required to acquire the other views at the desired SNR. Furthermore, attenuation data as a function of view angle is periodic with period of 180° and generally, peak attenuation value is a smooth function of view angle. Therefore, often, the peak attenuations from the planar views are used to determine an X-ray modulation function that varies harmonically as a function of view angle and has maximum and minimum values that are proportional respectively to the maximum and minimum peak attenuations of the planar views.

It is noted that whereas data from planar scans are used to determine modulation functions for reducing overall exposure of a patient to X-rays the planar scans themselves expose a patient to X-rays. It is also noted that irrespective of performing two planar scans for use in generating modulation functions, in general at least one planar scan of a patient is performed prior to the patient being CT-imaged to acquire data for determining position of a region of the patient to be CT-imaged.

U.S. Pat. Nos. 5,379,333, and 5,400,378 the disclosures of which are incorporated herein by reference describe acquiring "planar" data for a slice by imaging the slice at 0° and 90°. The planar data is used to determine a maximum value for $I_O$ for the slice and an X-ray modulation function that varies harmonically as a function of view angle.

U.S. Pat. No. 5,822,393 describes a method of adjusting a value for $I_O$ for a slice using a predicted maximum value for attenuation of X-rays in a projection of the slice. The predicted maximum attenuation is determined using a maximum attenuation measured from a projection for at least one preceding slice. The predicted attenuation is used to determine a value for $I_O$ for which, after $I_O$ is attenuated by the predicted maximum attenuation, a number of X-ray photons reaching an X-ray detector is greater than quantum noise of the detector.

SUMMARY OF THE INVENTION

An aspect of some embodiments of the present invention relates to providing an improved method for determining an X-ray modulation function for CT-imaging a region of a patient's body.

An aspect of some embodiments of the present invention relates to using known average values of absorption coefficients for different regions of the human body to provide data for the X-ray modulation function.

An aspect of some embodiments of the present invention relates to acquiring data for determining the X-ray modulation function, from a single planar scan of the patient.

An aspect of some embodiments of the present invention relates to a method of reducing an amount of X-ray radiation to which a patient is exposed during a planar scan of a region of the patient's body.

The inventors have noted that different regions of the human body can be characterized by different ranges for values of the absorption coefficient and that these ranges are substantially the same for all persons. Each region of the human body can therefore be characterized by an average value for the absorption coefficient that is substantially the same for all people. For example, the head region of all persons is generally characterized by an absorption coefficient $\mu(head)=(1.10\pm0.08)\mu(H_2O)$ where $\mu(H_2O)$ is the absorption coefficient for water. On the other hand, as a result of the presence of the lungs, the thorax of most persons is characterized by a relatively low absorption coefficient and $\mu(thorax)=(079\pm0.07)\mu(H_2O)$.

The inventors have also noted that within ranges for absorption coefficients applicable to people in general, sub-ranges for absorption coefficients exist that are determined by such factors as body type, gender and age. For example, for a given body region, mesomorphs will in general exhibit a larger average absorption coefficient for a body region than will endomorphs for a same body region. An average absorption coefficient for a particular body region of a person can therefore be defined more accurately than can be defined from an average for the general population, by taking into account the person's personal characteristics.

An average absorption coefficient for a particular region of the body is hereinafter referred to as a "characteristic absorption coefficient".

In accordance with some embodiments of the present invention, data for determining an X-ray modulation function for CT-imaging a region of a patient's body is provided using known characteristic values for absorption coefficients for the human body and dimensions of slices in the region.

In accordance with some embodiments of the present invention, prior to CT-imaging a region of a patient's body, a single planar scan of the region is preformed to acquire a single view of each slice in the region. Preferably, the planar scan is performed at either an anterior-posterior or lateral view angle, i.e. at substantially of 0° or 90° (or equivalently, at 180° or 270°). For convenience of exposition it is assumed that the view angle is 0°.

The data from the planar view of each slice is processed to determine a peak attenuation "$PA(0°,z)$" for the planar view and a width for the slice along an axis perpendicular to the direction of the planar view. For example, for the coordinate conventions used herein and for the 0° planar view, the direction of the planar view is along the y-axis (at 0° the X-ray source is located along the y-axis) and a width of the slice is determined along the x-axis. The width is determined, in accordance with an embodiment of the present invention, from positions of detectors in the array of detectors that register substantially non-zero values for X-ray attenuation at the view angle of the planar view.

In accordance with an embodiment of the present invention, a maximum value for the absorption integral $A(n,\theta,z)$ for the slice at a view angle of 90° is determined by multiplying the determined width of the slice along the x-axis by the characteristic absorption coefficient of the region of the patient's body in which the slice is located. The absorption integral is used to determine a peak attenuation $PA(90°,z)$ for the slice. The peak attenuations $PA(0°,z)$ (measured) and $PA(90°,z)$ (computed) are used to determine an X-ray modulation function for the slice.

In some embodiments of the present invention, intensity of X-rays used to perform a planar scan of a patient is adjusted in real time responsive to attenuation data acquired during the planar scan to minimize exposure of the patient to X-rays during the scan. As the planar scan is performed, data from a planar view of a slice is processed to determine a minimum X-ray intensity, $I_O$, that is sufficient to acquire attenuation measurements for the planar view at a desired SNR. The determined minimum intensity is used for acquiring a planar view for a next subsequent slice imaged in the planar scan. The intensity of X-rays used in performing the planar scan is thus constantly updated in real time to minimize intensity of X-rays to which the patient is exposed. It is noted, that in prior art, planar scans of patient are generally acquired at a constant X-ray intensity which is not adjusted to minimize X-ray exposure of the patient during the planar scan.

There is therefore provided, in accordance with an embodiment of the present invention, a method for determining a modulation function for modulating intensity of X-rays provided by an X-ray source of a CT-system for CT-imaging a slice of a region a person's body, the method comprising: acquiring X-ray attenuation data for a first substantially anterior-posterior or lateral view of the slice; determining a first maximum X-ray attenuation from the attenuation data; determining a length of a projection of the slice along an axis in the plane of the slice that is substantially orthogonal to the view angle using the attenuation data; determining a second maximum X-ray attenuation for a second view orthogonal to the first view based on the determined length; and using the first and second attenuation maxima to determine the modulation function.

Optionally, determining the second maximum X-ray attenuation comprises determining the second maximum to be equal to a product of the length of the projection multiplied by an average X-ray absorption coefficient of for the slice.

Optionally, the average X-ray absorption coefficient is equal to a predetermined average absorption coefficient characteristic of a region of the human body in which the slice is located.

Optionally the characteristic absorption coefficient is a function of at least one personal characteristic of the patient. Optionally, the at least one personal characteristic comprises the person's body-type. Optionally, the at least one personal characteristic comprises the person's gender. Optionally, the at least one personal characteristic comprises the person's age.

In some embodiments of the present invention, determining a length for the projection comprises: acquiring the first view with an array of X-ray detectors that face the X-ray source and that are located on a side of the body opposite to a side at which the X-ray source is located; determining first and second boundaries between detectors in the detector array that receive X-rays attenuated by material in the slice and detectors in the array that receive X-rays that are not attenuated by material in the slice; determining locations of projections of edges of the slice on the perpendicular axis from positions of the X-ray source at the first view angle and positions of detectors in neighborhoods of the first and second boundaries; and determining the length of the projection to be equal to a distance between the projections of the edges.

There is further provided in accordance with an embodiment of the present invention, a method of performing a planar scan of a region of a person's body utilizing a CT imager to acquire a planar view of each of a plurality of slices of the region comprising: illuminating each of the slices in the region with X-rays one after the other in order of their axial location along the body to acquire attenuation data for a planar view of each slice; and modulating intensity of X-rays used to illuminate the slices as a function of axial position to reduce exposure of the patient to X-ray radiation.

Optionally, the method comprises determining an X-ray intensity for illuminating at least one first slice of the plurality of slices responsive to data from a planar view of a previously illuminated at least one second slice.

Optionally, determining the X-ray intensity for the at least one first slice comprises: determining from the planar view of the at least one second slice a minimum X-ray intensity at which the at least one second slice should be illuminated to acquire attenuation data for the planar view of the at least one second slice at a desired signal to noise ratio; and determining the X-ray intensity at which the at least one first slice is illuminated responsive to the determined minimum intensity for the at least one second slice.

Optionally, the X-ray intensity for the at least one first slice is equal to the determined minimum intensity for a single second slice adjacent to the at least one first slice.

BRIEF DESCRIPTION OF FIGURES

Non-limiting examples of embodiments of the present invention are described below with reference to figures attached hereto. In the figures, identical structures, elements or parts that appear in more than one figure are generally labeled with a same numeral in all the figures in which they appear. Dimensions of components and features shown in the figures are chosen for convenience and clarity of presentation and are not necessarily shown to scale. The figures are listed below.

DETAILED DESCRIPTION OF EXEMPLARY EMBODIMENTS

Figure 1A:
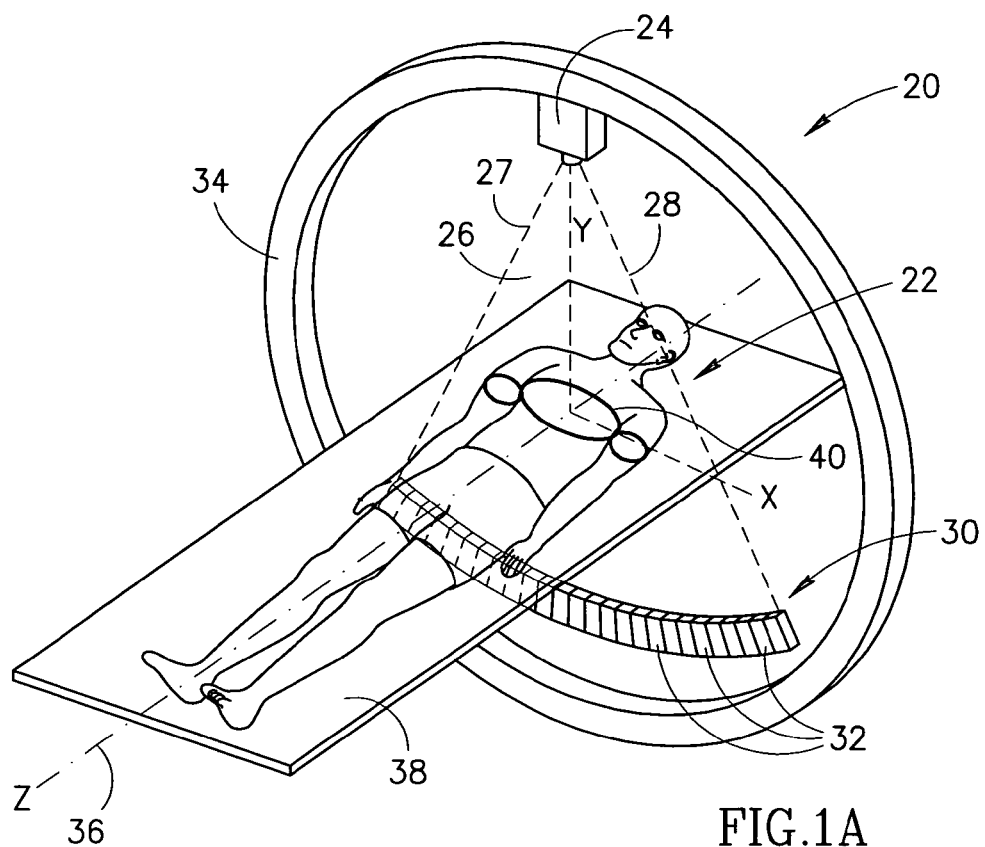
FIGS. 1A and 1B schematically show a third generation CT-system being operated to acquire data for generating an X-ray modulation function for controlling exposure of a patient to X-rays during CT-imaging of the patient with the CT-system, in accordance with prior art.
Figure 1B:
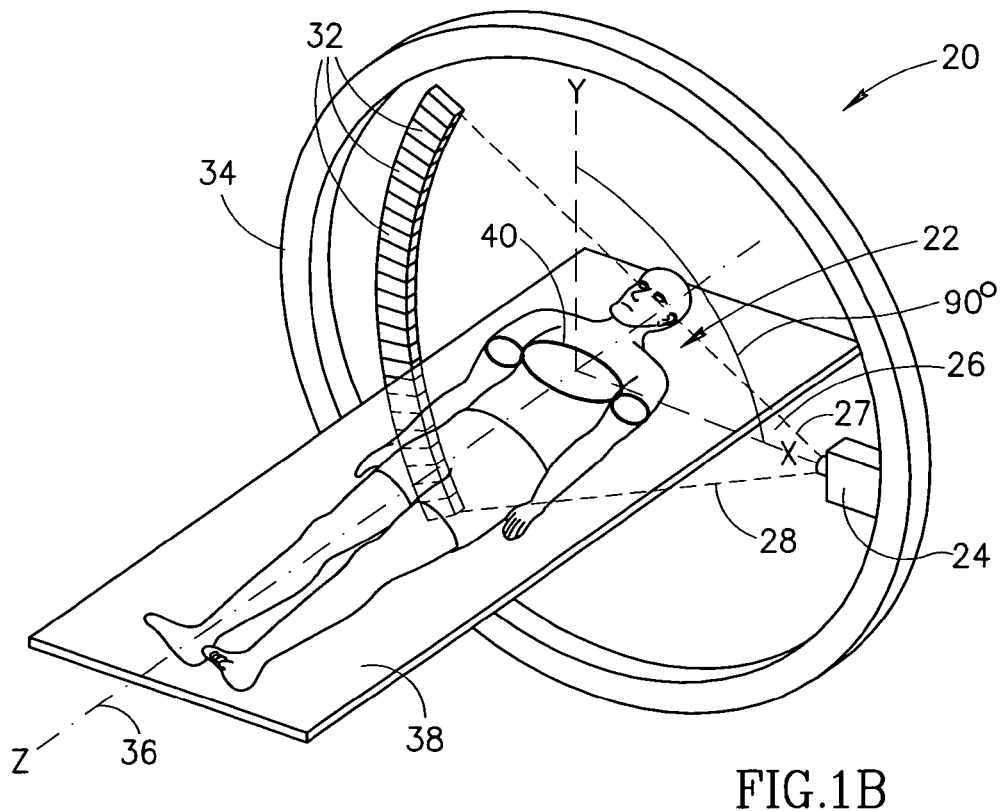

FIGS. 1A and 1B schematically show a third generation CT-system 20 being operated to acquire planar data for generating an X-ray modulation function to be used for controlling exposure of a patient 22 to X-rays during CT-imaging of a region of the patient's body with the CT-system. CT-system 20 is being operated in accordance with a typical prior art method to acquire the planar data. By way of example, the region to be imaged by CT-system 20 is a region of the chest of patient 22.

CT-system 20 comprises an X-ray source 24 controllable to provide a fan-beam 26 schematically indicated by dashed lines 27 and 28 and an array 30 of X-ray detectors 32 mounted opposite the X-ray source for sensing X-rays in the fan-beam. X-ray source 24 and detector array 30 are mounted in a gantry 34 so that the X-ray source and detector array can be rotated about an axis 36, either by rotating the gantry or by rotating the X-ray source and detector array within the gantry. Patient 22 is supported on a couch 38 during imaging of the patient with CT-system 20. Couch 38 is mounted on a suitable pedestal (not shown) so that couch 38 is controllable to be translated axially along axis 36. Detectors 32 in detector array 30 that would not normally be seen in the perspectives of FIGS. 1A and 1B are shown for clarity of presentation with ghost lines For convenience, a coordinate system having a horizontal x-axis, vertical y-axis and z-axis coincident with axis 36, is used to locate components and features of CT-system 20 and patient 22. The coordinate system is assumed to be fixed with respect to gantry 34. View angle of X-ray source 24 is measured with respect to the y-axis of the coordinate system. Slices of the body of patent 22 are located by the position of the slice along the z-axis. A z-coordinate of a slice is equal to an amount by which couch 38 must be translated to position the slice in the gantry so that a view of the slice can be acquired. Only components and features of CT-system 20 germane to the discussion are shown.

To acquire planar data for the region of patient 22, a first planar scan of the patient is performed to acquire planar views of slices of the patient that are located in the region at a view angle of 0°. In accordance with prior art, a second planar scan is then performed to acquire planar views of the slices in the region of interest at a view angle of 90°.

To perform the first scan, couch 38 is controlled to move the region of patient 22 along the z axis through gantry 34 while X-ray source 24 is positioned at 0°. As the region passes between the X-ray source and detector array 30, the X-ray source is controlled to illuminate slices in the region with X-rays having a constant intensity $I_O$ to acquire views of the slices. In FIG. 1A X-ray source 24 is shown illuminating a slice 40 of the patient in the region to acquire a planar view of the slice at a view angle of 0°. The second planar scan is performed similarly to the manner in which the first planar scan is performed but with X-ray source 24 positioned at a view angle of 90°. FIG. 1B schematically shows slice 40 shown in FIG. 1A being exposed to X-rays to acquire a 90° planar view of the slice.

Attenuation data acquired from the 0° planar view of slice 40 is processed to determine a suitably averaged minimum X-ray intensity $IM(0°,z)$ sensed by detectors 32 for the 0° planar view. The minimum is generally determined by analyzing X-ray intensity measurements as a function of detector identification index, after suitably smoothing the data using methods known in the art. A ratio $I_O/IM(0°,z)$ determines an average peak attenuation $PA(0°,z)$ for the slice. $I_O$, is determined from intensity of X-rays registered by a detector 32 for which X-rays do not pass through slice 40.

The average peak attenuation is then used to determine a minimum desired X-ray intensity "$I_O(0°)$" for which slice 40 is preferably exposed to properly image the slice at 0°. For example, assume that to provide a desired SNR for CT-imaging slice 40 at 0°, a minimum X-ray intensity detected by detectors 32 should be $I_D(0°,z)$. To provide the minimum detected intensity, slice 40 is preferably illuminated by X-ray source 24 with X-rays at intensity $I_O(0°,z)=I_D(0°,z)$ $PA(0°,z)$.

A similar procedure is used to determine a minimum desired intensity "$I_O(90°,z)$" from attenuation data provided by the planar view of slice 40 at 90°.

$I_O(0°,z)$ and $I_O(90°,z)$ are then used, in accordance with methods known in the art to generate a suitable modulation function for determining X-ray intensity $I_O(\theta,z)$ to be provided by X-ray source 24 for acquiring views of slice 40 as a function of view angle. For example $I_O(\theta,z)$ may be defined so that $I_O(\theta,z)=I_O(0°,z)\cos^2(\theta)+I_O(90°,z)\sin^2(\theta)$, or $I_O(\theta,z)=0.5[I_O(0°,z)+I_O(90°,z)]+0.5[(I_O(0°,z)-I_O(90°,z)]\cos(2\theta)$.

Unlike the prior art method described above, in which planar data for a region of the body of patient 22 is acquired from two planar scans of the region, in accordance with an embodiment of the present invention, planar data for the region of patient 22 is acquired from only a single planar scan of the region.

The single planar scan is preferably acquired for a view angle of 0° or 90°, or equivalently for a view angle of 180° or 270°. For convenience, the view angle for the single planar scan is assumed to be 0°. Acquisition of planar views for slices in the region of interest are, optionally, acquired similarly to the way in which planar views of the slices are acquired in prior art, as shown in FIG. 1A. And, in accordance with an embodiment of the present invention, attenuation data from each 0° planar view of a slice at axial position z is processed similarly, as described above, to provide a value for $I_O(0°,z)$.

However, unlike in prior art, in accordance with an embodiment of the present invention, attenuation data acquired for the planar view of slice 40 at view angle 0° is also used to provide information for determining $I_O(90°,z)$ as well.

Figure 2:
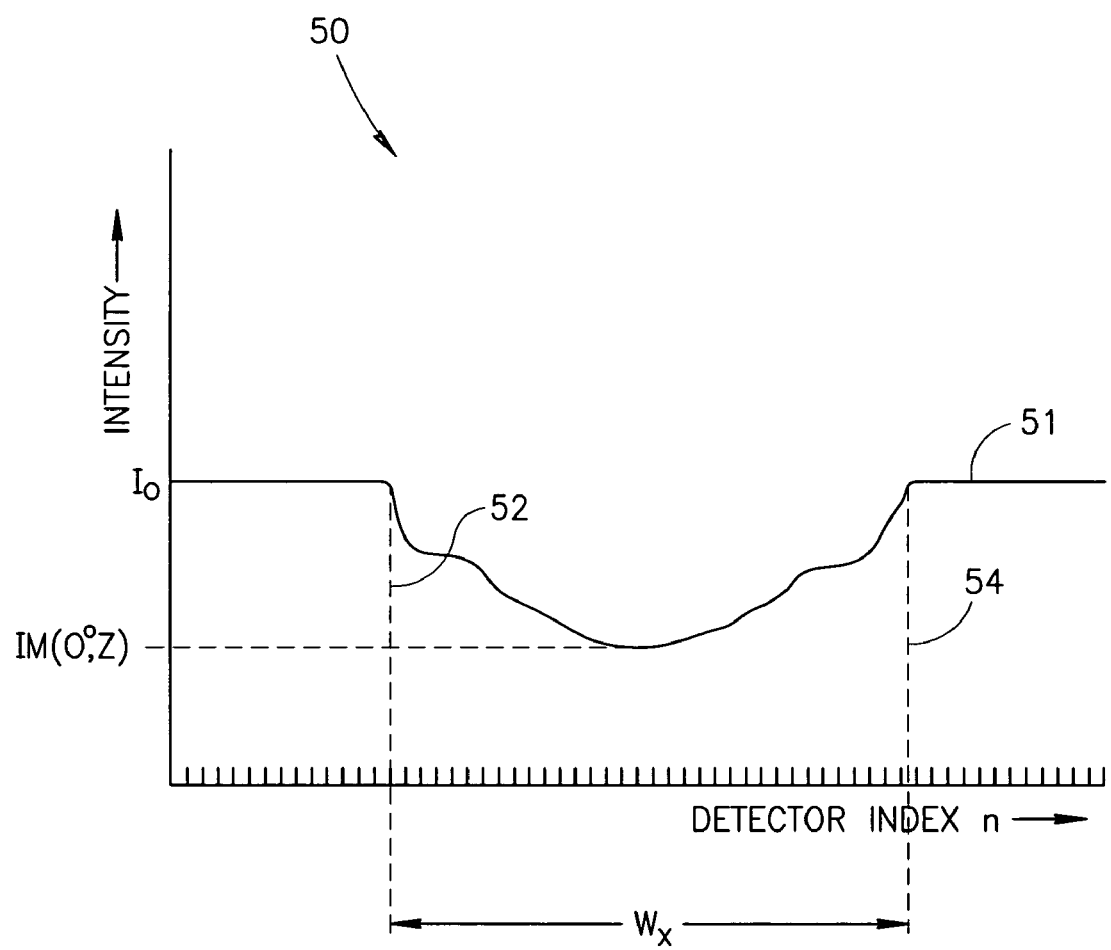
FIG. 2 shows a graph of schematic attenuation data taken at an anterior-posterior (0°) view of a slice of the patient shown in FIG. 1A, that schematically illustrates how attenuation data from a single planar view is used to determine information for a modulation function, in accordance with an embodiment of the present invention.

FIG. 2 shows a graph 50 in which intensity $I(n,0°,z)$ of X-rays detected by detectors 32 for the 0° planar scan of slice 40 shown in FIG. 1A is schematically shown by a curve 51 as a function of index n which identifies different detectors 32 in detector 30. Detectors 32 that receive X-rays from X-ray source 24 that are not attenuated by passing through slice 40 register an intensity $I_O$, which is intensity of X-rays provided by the X-ray source. In accordance with an embodiment of the present invention, the data is assumed to have been filtered with an appropriate smoothing filter.

A minimum detected intensity $IM(0°,z)$ is identified from curve 51 and is indicated on the ordinate of the graph. As described above, $IM(0°,z)$ is used to determine an average peak attenuation and a desired minimum X-ray intensity at which slice 40 should be exposed to provide a 0° view of the slice when the region of patient 22 is imaged by CT-system 20.

To determine $I_O(90°,z)$, in accordance with an embodiment of the present invention, the data shown in graph 50 is also analyzed to determine a width "Wx" for slice 40 along the x-axis. Wx is determined by analyzing the data to determine boundaries between detectors 32 for which sensed X-ray intensity indicates that X-rays reaching the detectors are substantially unattenuated by material in slice 40 and detectors 32 for which sensed intensity indicates that X-rays reaching the detectors are attenuated by material in the slice.

For the data shown in graph 50 the boundaries are indicated by dashed lines 52 and 54. Detectors in the region of boundaries 52 and 54 detect X-rays that pass through regions of slice 40 in the neighborhood of edges of the slice. In accordance with an embodiment of the present invention, positions of detectors in the region of boundaries 52 and 54 that indicate attenuation, and known positions of these detectors relative to X-ray source 24, are used to determine x coordinates of the edges of slice 40. From the x coordinates of the edges a width $W_X$ is determined. In graph 50, $W_X$ is schematically shown as spanning boundaries 52 and 54.

The determined $W_X$ is multiplied by the known average absorption coefficient characteristic of the region of the body of patient 22 in which slice 40 is located to provide an estimate for a maximum value for the absorption integral AI(n, 90°,z) for the 90° view of the slice.

It is noted that the characteristic absorption coefficient used to provide the maximum value for AI(n, 90°,z), may be a characteristic absorption coefficient determined for the general population or might be a characteristic absorption coefficient relevant for a particular subgroup of the general population to which patient 22 belongs. For example, the characteristic absorption coefficient may be determined by the gender, age or body type of patient 22.

Let AIM(90°,z) represent the maximum value for the absorption integral for 90°. Then, in accordance with an embodiment of the present invention, AIM(90°,z)=$\mu(z)W_X$, where $\mu(z)$ is the characteristic absorption coefficient for the body region at the z coordinate of slice 40. AIM(90°,z) is used to determine an average peak attenuation PA(90°,z)= exp(−AIM(90°,z))=exp(−$W_X\mu(z)$). As above, PA(90°,z) and a desired minimum detected intensity ID(90°,z) at detector array 30 for view angle 90° are used to determine a desired minimum intensity $I_O$(90°,z) so that $I_O$(90°,z)=$I_D$(90°,z)PA(90°,z)=$I_D$(90°,z) exp($W_X\mu(z)$). In FIG. 1A, slice 40 is located in the chest region of patient 22. For the chest region the characteristic absorption coefficient has a value of (0.79±0.07)$\mu(H_2O)$ so that for slice 40, $I_O$(90°,z) is estimated as being equal to $I_D$(90°,z) exp[$W_X$(0.79)$\mu(H_2O)$].

In some embodiments of the present invention, to reduce exposure of patient 22 to X-rays during the 0° planar scan intensity of X-rays used to perform the planar is adjusted in real time responsive to attenuation data acquired during the planar scan. Data acquired from a 0° planar view obtained during the planar scan of one slice is used to determine a minimum X-ray intensity required to expose a next slice to acquire a 0° planar view of the next slice. X-ray intensity during the planar scan is thereby updated in real time to reduce radiation exposure of the patient.

For example, assume that a 0° planar view is acquired at X-ray intensity $I_{o1}$ for a slice at coordinate $z_1$ and that after processing data from the planar view it is determined, for example from PA(0°,$z_1$), that data for the planar view could have been acquired at a desired SNR at minimum X-ray intensity $I^*_{o1} < I_{o1}$. Then, in accordance with an embodiment of the present invention, a next adjacent slice at coordinate $z_2$ is exposed to X-ray intensity $I^*_{o1}$ to acquire a 0° planar view for the slice. It is noted, that in prior art, planar scans of a region of a patient's body are generally acquired at a constant X-ray intensity which is not adjusted to minimize X-ray exposure of the patient during the planar scan.

In some embodiments of the present invention a minimum intensity at which a planar scan of a "next adjacent slice" is acquired is determined from minimum X-ray intensities determined for a plurality of previously illuminated slice. For example, in some embodiments of the present invention X-ray exposure intensity for a "next adjacent slice" is determined to be equal to a minimum intensity predicted from a curve fit to the minimum X-ray intensities determined for a plurality of previously exposed slices or an average.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

The invention claimed is:

1. A method for determining a modulation function for modulating intensity of X-rays provided by an X-ray source of a CT-system for CT-imaging a slice of a region a person's body, the method comprising:
   acquiring X-ray attenuation data for a first substantially anterior-posterior or lateral view of the slice;
   determining a first maximum X-ray attenuation from the attenuation data;
   determining a length of a projection of the slice along an axis in the plane of the slice that is substantially orthogonal to the view angle using the attenuation data;
   determining a second maximum X-ray attenuation for a second view orthogonal to the first view based on the determined length; and
   using the first and second attenuation maxima to determine the modulation function.

2. A method according to claim 1 wherein determining the second maximum X-ray attenuation comprises determining the second maximum to be equal to a product of the length of the projection multiplied by an average X-ray absorption coefficient of for the slice.

3. A method according to claim 2 wherein the average X-ray absorption coefficient is equal to a predetermined average absorption coefficient characteristic of a region of the human body in which the slice is located.

4. A method according to claim 3 wherein the characteristic absorption coefficient is a function of at least one personal characteristic of the patient.

5. A method according to claim 4 wherein the at least one personal characteristic comprises the person's body-type.

6. A method according to claim 4 wherein the at least one personal characteristic comprises the person's gender.

7. A method according to claim 4 wherein the at least one personal characteristic comprises the person's age.

8. A method according to claim 1 wherein determining a length for the projection comprises:

acquiring the first view with an array of X-ray detectors that face the X-ray source and that are located on a side of the body opposite to a side at which the X-ray source is located;

determining first and second boundaries between detectors in the detector array that receive X-rays attenuated by material in the slice and detectors in the array that receive X-rays that are not attenuated by material in the slice;

determining locations of projections of edges of the slice on the perpendicular axis from positions of the X-ray source at the first view angle and positions of detectors in neighborhoods of the first and second boundaries; and determining the length of the projection to be equal to a distance between the projections of the edges.

* * * * *